United States Patent [19]
Miller

[11] Patent Number: 5,606,167
[45] Date of Patent: Feb. 25, 1997

[54] CONTRABAND DETECTION APPARATUS AND METHOD

[76] Inventor: Thomas G. Miller, 254 Brentwood La., Madison, Ala. 35758

[21] Appl. No.: 380,953

[22] Filed: Jan. 31, 1995

Related U.S. Application Data

[63] Continuation-in-part of Ser. No. 273,404, Jul. 11, 1994.

[51] Int. Cl.$^6$ .................................................. G01N 23/09
[52] U.S. Cl. ............................. 250/390.04; 250/390.05; 250/390.06; 250/390.07; 250/390.08; 250/390.11; 250/390.12
[58] Field of Search .................. 250/390.04, 390.05, 250/390.06, 390.07, 390.08, 390.11, 390.12

[56] References Cited

U.S. PATENT DOCUMENTS

| | | | |
|---|---|---|---|
| 5,200,626 | 4/1993 | Schultz et al. ..................... | 250/390.04 |
| 5,410,156 | 4/1995 | Miller ................................. | 250/390.04 |

OTHER PUBLICATIONS

Conrad Doose, Engelbert Hanning and Rolf Stockmeyer, "A large neutron time-of-flight spectrometer with air pad supports," *Kerntechnik* vol. 17, No. 12 (1975) pp. 540–545.

*Primary Examiner*—Constantine Hannaher

[57] ABSTRACT

A contraband detection system (18) using a single, cone shaped neutron beam determines substances concealed in a sample object by developing total neutron cross section spectra for a plurality of elements, including carbon, nitrogen, oxygen, hydrogen and other potential contraband-indicating elements. A processor (26) performs a contraband determination classification based on the neutron total cross section spectra for the plurality of elements, including hydrogen and elements which do not have peaks in the energy range of interest. The contraband detection system (18) includes a neutron source (20) for producing a pulsed, cone shaped beam of fast white neutrons; a spatial neutron detection array (40); a conveyor system (28) for situating a sample object (29) between the source (20) and the detection array (40); a spectra analysis system (24) for determining the neutron total cross section spectra of elements located in the sample object; and the processor (26). The neutron source (20) produces a pulsed beam (36) of fast white neutrons having sufficient energy range whereby removal of neutrons from the beam caused by the presence of a plurality of contraband-indicating elements can be determined. Various techniques of making contraband classification determinations are also disclosed.

20 Claims, 7 Drawing Sheets

| Regression Statistics | |
|---|---|
| Multiple R | 0.997032383 |
| R Square | 0.994073572 |
| Adjusted R Square | 0.993987682 |
| Standard Error | 0.016680948 |
| Observations | 281 |

Analysis of Variance

| | df | Sum of Squares | Mean Square | F | Significance F |
|---|---|---|---|---|---|
| Regression | 4 | 13.19253535 | 3.298133838 | 11573.76386 | 6.1078E-306 |
| Residual | 276 | 0.078650727 | 0.000284966 | | |
| Total | 280 | 13.27118608 | | | |

| | Coefficients | Standard Error | t Stat | P-value | Lower 95% | Upper 95% |
|---|---|---|---|---|---|---|
| Intercept | 0.023397016 | 0.006655811 | 3.51527654 | 0.000513297 | 0.010294408 | 0.036499624 |
| H | 0.102390929 | 0.001703072 | 60.12131203 | 1.3199E-160 | 0.099038267 | 0.105743591 |
| C | 0.046817924 | 0.003444122 | 13.5935746 | 1.44495E-32 | 0.040037838 | 0.053598011 |
| N | 0.069203613 | 0.002402192 | 28.80852352 | 3.58015E-85 | 0.064474665 | 0.073932561 |
| O | 0.076622773 | 0.000761344 | 100.6414962 | 1.4276E-219 | 0.075123994 | 0.078121552 |

Fig. 7

CONTRABAND DETECTION APPARATUS AND METHOD

CROSS REFERENCE TO RELATED APPLICATIONS

This application is a continuation-in-part of U.S. patent application Ser. No. 08/273,404, "Contraband Detector Apparatus and Method," filed Jul. 11, 1994. In addition, this application has similarities with Miller, (U.S. Pat. No. 5,410,156), issued on Apr. 25, 1995.

FIELD OF INVENTION

This invention pertains to the detection of contraband and particularly to the detection and identification of explosives and illicit drugs concealed in luggage and the like.

PRIOR ART AND OTHER CONSIDERATIONS

Small amounts of modern explosives are easy to hide in airport luggage, cannot be detected by current systems, and can destroy an airplane. A workable system for detecting explosives in airport luggage is urgently needed. The most accurate method would be to identify the number densities of elements throughout the luggage. The ratios obtained from these number densities could be used to identify explosives with great precision. For practical use in an airport, each scan would have to be completed in seconds. A system this advanced does not exist and is not possible under current technology.

Current methods for detecting explosives in airport luggage use neutral particle probes, such as X-rays and neutrons, which can penetrate sealed luggage. However, existing systems cannot identify all of the elements which comprise explosives and have other shortcomings noted below.

X-ray systems are sensitive to differences in X-ray absorption coefficients in luggage. Because explosives have absorption coefficients similar to items commonly found in luggage, X-ray systems, including X-ray computed tomography (CT) scanners, have high false alarm rates.

Thermal neutron absorption (TNA) detects the n,γ reaction on nitrogen and so searches only for nitrogen. Since many non-explosive items found in luggage are rich in nitrogen, TNA has an unacceptably high false alarm rate. Other problems with TNA include that the neutrons must be thermalized, the n,γ cross section is in the millibarn range, it is difficult to obtain the spatial nitrogen concentration, and the background count rate is very high. "Explosive Detection System Based on Thermal Neutron Activation", IEEE AES Magazine, December 1989 and "Nuclear-Based Techniques for Explosive Detection", T. Gozani, R. Morgado, C. Seher, Journal of Energetic Materials, Vol. 4, pp. 377–414 (1986).

Pulsed fast neutron absorption (PFNA) detects the inelastic scattered gamma rays from nitrogen, carbon, and oxygen. Problems with PFNA include that the cross sections are in the millibarn range, background count rates are very high, determination of concentration as a function of position has large uncertainties, and it is difficult to make a gamma ray detector with adequate energy resolution and still maintain high count rate capability. "PFNA Technique for the Detection of Explosives", Proc. of First-Int. Sym. on Explosives Det. Technology, FAA Tech. Ctr., Atlantic City Int. Airport, N.J., Feb. 1992.

Grenier discloses a system based upon the n,γ reaction with pulsed 14 MeV neutrons. Grenier (U.S. Pat. No. 4,882,121). Grenier's system uses the inelastic scattering cross section or partial cross section. Since total cross sections are generally 100 to 1000 times larger than inelastic cross sections, a system based on total cross sections would be much more effective than Grenier's system. Grenier's system is based upon secondary interactions (detecting gamma rays resulting from first order interactions), would require a long counting time, and does not give hydrogen concentrations.

As noted above, existing nuclear-based systems search for explosives in indirect ways, such as detecting gamma rays emitted from neutron interactions. A system is needed which can probe directly for explosives through first order interactions. The most accurate method would be to identify the number densities of the elements which make up explosives. Using a fast neutron probe in a neutron transmission/ attenuation system would be ideal, because the neutrons can penetrate the sample and interact directly with the atoms.

The Federal Aviation Administration Guidelines list numerous nuclear techniques for detecting explosives in luggage. "Guidelines for Preparing Responses to the Federal Aviation Administration's Broad Agency Announcement for Aviation Security Research Proposals, Revision 3, Nov. 1, 1989" (the "Guidelines"). The Guidelines only briefly describe a fast neutron attenuation technique:

A broad energy spectrum of pulsed neutrons is created. The elements in the path of the beam absorb those neutrons whose energies correspond to the characteristic neutron resonances of the elements. The dips in intensity spectrum of the neutrons that pass through the luggage, measured as a function of the beam position, yield a projected image of the elemental distribution in the bag. This method was published several years ago. It has not been applied to the airport security problem.

Guidelines Section 1.1.3.6 at page 7 (emphasis supplied). The technique described in the Guidelines is not optimal, for reasons described below.

The Guidelines state that "some of the methods measure only nitrogen; . . . the other methods seek to measure all other major elements in an explosive, carbon, oxygen, and nitrogen, by using fast neutrons for the interrogation." Guidelines at page 5 (emphasis added). The Guidelines technique searches only for elements which "absorb" neutrons corresponding to the characteristic neutron resonances of carbon (C), nitrogen (N) and oxygen (O). The Guidelines technique is based upon the absorption or partial cross section rather than the total cross section. However, the C, N and O would "absorb" only a small percentage of neutrons in the beam: only those neutrons with energies which are close to the resonance peaks of the elements in the beam. Hence the Guidelines technique could measure only a small percentage of neutron interactions, which would negatively affect both the statistics and the time required to complete a scan.

A technique which uses the total neutron cross section would be more effective than the Guidelines technique. A system based on the total cross section would provide better statistics, would be more accurate, and would allow faster scanning. For example, consider the 1 MeV oxygen peak. The absorption cross section at 1 MeV is at most a few millibarns. In contrast, the total cross section is approximately 8.21 barns. Other resonance peaks give similar ratios between their resonance absorption cross sections and the total cross section. The resonance absorption cross sections are in the millibarn range while the total cross sections are in the barn range.

Also, the Guidelines technique cannot detect hydrogen (H), since H does not have a resonance peak. Knowledge of the distribution of H in a sample would be useful in identifying explosives and other contraband. A system using the total cross section, and which can detect H as well as C, N and O, would be a significant improvement over the technique described in the Guidelines.

In addition, the Guidelines technique is not optimal for use in an airport or for any use which requires a fast scan. The Guidelines describe a technique which scans a neutron beam across a suitcase and determines the location of the explosive "as a function of the beam position". In order to locate an explosive "as a function of the beam position", a system must scan the beam over numerous positions across the suitcase, identify the elements in the beam at each position, analyze for an explosive at each position, and identify the beam position relative to the luggage at the time an explosive is detected. Since small explosives can cause extensive damage, the beam must scan in small increments. This would require numerous scans over a single piece of luggage. A system which scanned an entire sample at the same time would be a significant improvement to the Guidelines technique.

The Guidelines note that fast neutron attenuation has not been applied to airport security. Fast neutron attenuation has been applied to determine the composition of agricultural products, applications which do not require fast scanning or position sensitive detection. "Determination of H, C, N, O Content of Bulk Materials from Neutron-Attenuation Measurements," by J. C. Overley, Int. J. Radiat. Isot., Vol 36, No. 3, pp. 185–191, 1985. "Element-Sensitive Computed Tomography with Fast Neutrons" by J. C. Overley, Nuclear Instruments and Methods in Physics Research, B24/25 (1987) pp. 1058–1062. Overley's work used small (2 cm) collimated neutron beams and required a considerable amount of time (10 minutes) to complete a scan at each location of the beam. In order to scan a suitcase 60 cm by 75 cm, Overley's method would require hours. In contrast, an airport security system requires that an entire suitcase be scanned in 10 seconds or less. Overley's technique is based upon numerous scans of a single sample by one or more neutron beams, could not operate in an airport or other environment requiring a fast scan, and is recognized by Overley as unworkable under current technology.

Overley did not describe a workable technique for contraband detection. However, the technique described by Overley was a logical extension of his collimated beam method, or the use of multiple beams from a single accelerator to scan bulk material:

Capital equipment requirements probably restrict practical application of the technique at the present time. Special purpose accelerators are beginning to evolve, however, and the possibility of producing several neutron beams simultaneously from one machine may reduce this impediment in the future.

Overley (1985) at 191 (emphasis supplied). One of the limitations of current technology is that existing accelerators do not produce multiple beams. Even if a multiple beam accelerator is developed, it is doubtful that it could produce enough beams for practical use in a contraband detection system. For example, to cover an entire suitcase in a single scan would require hundreds of beams. Overley recognized these limitations under current technology when stating that the method is not of practical application at this time. Over a decade after publication of Overley's work, as noted in the Guidelines, a workable system has not been developed which can apply fast neutron attenuation to detect explosives and other illicit contraband in airport luggage.

A system using only one neutron beam to scan an entire sample at one time would be an improvement over current proposals, which would use multiple beams or multiple scans. However, a single beam, single scan system would require solutions to several problems that are not obvious and are not anticipated by the Guidelines, Overley, or other references.

One problem unsolved under current technology in creating a single beam, single scan system relates to the neutron probe. The methods outlined by Overley and the Guidelines use one or more collimated neutron beams. In contrast, a single beam, single scan system requires an uncollimated beam which expands in a cone shape, so that a sample object can be placed at the arc at the end of the cone for coverage by the single beam. A single beam, single scan system should use a neutron beam with an angular distribution of neutrons relatively flat around 0 degrees. This flat angular distribution would be required in order to obtain constant statistics across the sample.

Another problem unsolved under current technology in creating a single beam, single scan system relates to the detection system. A system using a single cone shaped beam to scan luggage in a single pass requires a detection system which can detect small amounts of explosives and pinpoint their location in the luggage. A workable detection system would require numerous detectors with a relatively small spatial resolution. For example, a 4 cm by 4 cm spatial resolution is generally required in order to locate lethal amounts of explosives. To cover a 60 cm by 80 cm suitcase, a system would require approximately 300 detectors. In general, the detector array would be even larger to cover larger containers or to cover containers with a smaller spatial resolution (perhaps up to 625 detectors). Each detector would require its own electronics. A system using 625 discrete detectors requires 625 electronics systems, processes hundreds of thousands of neutron interactions per second, and has only 10 seconds (or less) to complete a scan of an entire suitcase, analyze the elemental distributions in the suitcase, make a classification regarding contraband, and sound an alarm. The large number of detectors would require optimizing the electronics and data analysis systems. A detection system meeting these requirements does not exist.

Another unsolved problem in developing a single beam, single scan system under current technology is configuration for neutron time of flight measurements. As noted above, the detection system must be optimized in order to handle hundreds of thousands of neutron detection events over hundreds of detectors and include time of flight measurements. Simply stacking neutron detectors into a two-dimensional (x–y) array would allow detection of neutrons over increments of a sample placed between the beam and the detector array. However, an x–y array would cause neutrons of the same energy to register different times of flight for each detector, since the distance from the neutron source to each detector would vary. At a minimum this would require complex electronics and calculations which would correct every detector for every detection event. This problem is significant, since, as noted above, a single beam, single scan system would require many detectors and must be optimized.

While x–y detectors have been constructed for thermal neutrons, such detectors could not be used in a fast neutron attenuation system. In general, thermal neutron detectors cannot be used to detect fast neutrons due to the lower detection efficiency. These detectors allow thermal neutrons to interact with an element that has a large fission cross section. A CCD camera placed outside the thermal neutron beam records the resulting scintillation and its position. E. W. McFarland, R. C. Lanza and G. W. Poulos, "Multi-dimensional Neutron-computed Tomography Using Cooled, Charge-Coupled Devices," IEEE Transactions on Nuclear Science, Vol. 38, No. 2, April 1991. A variation includes a neutron camera, which also must be used with thermal neutrons. Sulcoski and Brenizer "Neutron Radiography" by John P. Barton, 753–760, D. Reidell Publishing Company, Boston, 1986. Another variation uses an element that absorbs the thermal neutrons and emits x-rays or gamma rays, which are detected with film or scintillation sensors. Crispin, Roberty and Reis "Neutron Radiograph" by S. Fujinne, 865–872, Kluwer Academic Publishers, London, 1989.

The above types of x–y detectors will not satisfy the requirements for a fast neutron detector. A principal reason is that the cross section for fission is very small for fast neutrons and fission detectors have a very low efficiency. Also, such detectors are not configured for time of flight measurements.

X–y detectors for fast neutrons do exist, but cannot be used for time of flight or neutron attenuation measurements. One type is the multi-wire proportional counter (MWPC) with a proton radiator at the entrance to the MWPC. *"Neutron Radiography"* by John P. Barton, 829–836, D. Reidell Publishing Company, Boston, 1986.; K. H. Valentine, S. Kaplan, V. Perez-Mendez and L. Kaufman, "A Multi-wire Proportional Chamber for Imaging Thermal, Epicadmium, and Fast Neutrons" IEEE Tr. on Nucl. Sc., Vol. NS 21, NO. 1, 1974, 178–183; B. Director, S. Kaplin and V. Perez-Mendez, "A Pressurized Multi-Wire Proportional Chamber for Neutron Imaging," IEEE Tr. on Nucl. Sc., Vol. NS-25, No. 1, Feb. 1978, 588–561. The MWPC consists of thin gas filled cells with small wires running parallel through the cells. The wires are s placed at high voltage and when a proton enters the cell close to a particular wire, a voltage pulse is created. By recording the position of the voltage pulse from a particular wire, the position of the event is known in the direction perpendicular to the wires. By placing a second ionization chamber with wires running perpendicular to the first set of wires, the position in the other direction is determined.

A basic problem with this type of fast neutron detector is that the radiators must be very thin so that the recoil protons can escape from the radiator. In order to achieve reasonable efficiencies, many of these units must be placed in tandem. This problem is compounded when counting neutrons below 3 MeV. This is because the radiator would need nearly zero width for the lower energy protons to get through the first cell, making the efficiency near zero.

De Volpi discloses a method for high-resolution radiography by using gamma rays or neutrons and a hodoscope. De Volpi (U.S. Pat. No. 4,092,542). De Volpi's system measures changes in the density of sample materials and is not workable in a neutron attenuation system using time of flight measurement. Also, De Volpi uses nuclear reactors as his source of neutrons and so the neutrons are in the KeV energy range or lower. Although De Volpi does not mention the type of neutron detector, detectors for KeV energy neutrons and lower energies generally are not useful for detecting neutrons in the MeV energy range. Neutron detectors for a workable fast neutron attenuation system must be capable of nanosecond timing resolution. There is no such timing requirement for De Volpi's patent. While De Volpi apparently stacks detectors vertically, the detection system is not configured for time of flight and no discussion is provided regarding the detection system.

Another class of x–y fast neutron detectors uses a number of photomultiplier tubes placed behind a scintillator. Strauss (U.S. Pat. No. 4,454,424). When neutrons are incident on the scintillator, some of the neutrons are absorbed and cause scintillations via fission. The recoil fission fragments create pulses of light which are detected by the photomultiplier tubes. The x–y position of the neutron interaction is determined by the particular photomultiplier tube which senses the light pulse. The Strauss detector uses a glass scintillator loaded with Lithium-6, which is not sensitive to fast neutrons. The Strauss detector does not measure neutron energy. The Strauss detector measures neutron interactions only on an x–y plane and so is not appropriate for use in a fast neutron attenuation system requiring time of flight measurements.

Broadhurst (U.S. Pat. No. 5,278,418) discloses a technique to detect nitrates in a sample. Broadhurst's system detects only nitrogen and oxygen. Broadhurst's technique involves creating an energy variant neutron beam for measurement of neutron transmissions on and off the neutron resonances of nitrogen and oxygen. In this way, the Broadhurst technique seeks to infer the amount of nitrogen and oxygen present in a suitcase. Hence the Broadhurst technique measures the neutron attenuation over a very small energy interval using complicated equipment. A much better technique would be to measure the neutron attenuation over an energy range of several MeV.

Gomberg discloses an explosive detection system based only on elastic scattering cross sections. Gomberg (U.S. Pat. No. 4,864,142). Gomberg describes a low count rate system because neutrons scatter at all angles, and his detectors are placed at back angles and so intercept only a small fraction of the scattered neutrons. Gomberg's neutron source must be varied from 0.1 to 4.2 MeV, which is a complicated procedure and cumbersome to implement. An airport system based on Gomberg's method could take hours to scan a single piece of luggage.

In summary, no existing contraband detection system applies fast neutron attenuation over a broad energy range to identify explosives. Existing proposals are based upon multiple beams or multiple scans of a sample. No existing or proposed technique would allow detection of contraband-indicating elements which do not have a resonance peak, such as hydrogen. Current technology would allow only multiple scan or multiple beam systems, which, even if developed in the future, would be impractical for any use requiring a fast scan. Existing types of x–y detectors will not allow the accurate time of flight measurements required by a fast neutron attenuation system. Current technology and prior art do not teach how a fast neutron attenuation system could be built to solve these problems.

OBJECTS

Accordingly, it is an advantage of the present invention to provide an accurate and fast method and apparatus for detecting and identifying contraband substances.

Another advantage of the present invention is to allow all portions of a sealed container to be analyzed simultaneously, by applying a single, cone shaped neutron beam.

Still another advantage of the present invention is the use of the total neutron cross section to detect contraband.

Yet another advantage of the present invention is the detection of contraband having small mass.

Yet another advantage of the present invention is detection of hydrogen, which does not have a resonance peak.

An additional advantage of the present invention is a method and apparatus for allowing time of flight measurement of neutrons over a multi-dimensional curved plane (R-θ-φ with constant R).

SUMMARY

A contraband detection system produces a single, cone shaped, pulsed white neutron beam with a relatively flat neutron angular distribution around zero degrees. A sample is placed in the beam at a point at which the beam has expanded sufficiently to cover the entire sample, allowing a simultaneous scan of the entire sample. The transmitted beam is then examined and compared to the original beam. The contraband detection system determines substances concealed in a sample object (such as luggage) by using the neutron total cross section spectrum for hydrogen and a plurality of other elements, including nitrogen, oxygen and carbon. A processor performs a contraband determination classification based on the spectra for the plurality of elements. The contraband detection system measures the neutron attenuation spectra for the sample and, using the total cross sections, determines the number densities of carbon, nitrogen and oxygen which possess resonance peaks, and provides the number density for hydrogen which does not have a resonance peak.

The contraband detection system includes a neutron point source for producing a pulsed beam of fast white neutrons in the shape of a cone with a relatively flat neutron distribution around 0 degrees; a spatial neutron θ-φ detection array (R-θ-φ with constant R), which records fast neutrons at neutron energies from approximately 0.5 MeV to beyond 15 MeV; means for situating a sample object between the source and the detection array; a spectra analysis system for determining the neutron attenuation spectra of substances located in the sample object; and the classification processor.

The neutron point source produces pulsed fast white neutrons having a sufficient energy range whereby removal of neutrons from the beam (by absorption or scattering) caused by a plurality of contraband-indicating elements is used to determine the neutron attenuation spectra of a sample object.

The θ-φ detector array comprises an array of neutron detector elements arranged to form a curved surface. Each of the detector elements is aligned along a neutron path with a corresponding three-dimensional sector of the sample object, whereby a two-dimensional coordinate of the location of contraband in the sample object can be specified. In one embodiment, the surface of the detector array is in the shape of a portion of a sphere, so that all detectors in the array are equidistant from the neutron point source. Various techniques of making a contraband classification determination are also disclosed.

BRIEF DESCRIPTION OF THE DRAWINGS

The foregoing and other objects, features, and advantages of the invention will be apparent from the following more particular description of preferred embodiments, as illustrated in the accompanying drawings in which reference characters refer to the same parts throughout the various views. The drawings are not necessarily to scale, emphasis instead being placed upon illustrating the principles of the invention.

FIG. 7 gives the regression theory statistics for the curve fit of FIG. 6.

DETAILED DESCRIPTION OF THE DRAWINGS

Figure 1:
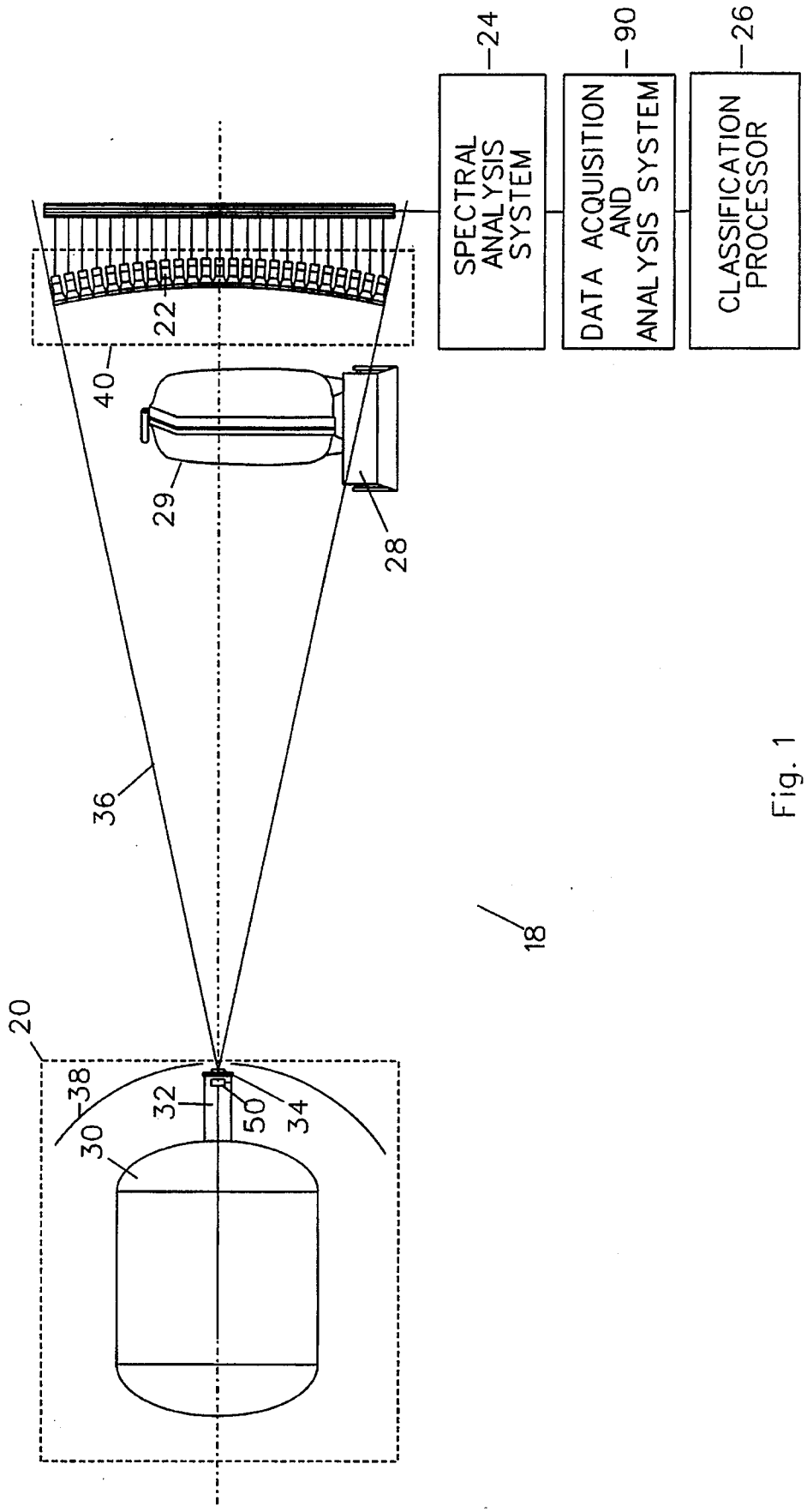
FIG. 1 is a schematic view of a detection system according to an embodiment of the invention.

FIG. 1 shows a contraband detection system 18 including a neutron source 20; a neutron detector assembly 22; a spectra analysis system 24; and, a classification processor 26. FIG. 1 also shows a conveying system 28 for introducing a sample object 29, such as a suitcase, between the neutron source 20 and the neutron detector assembly 22.

The neutron source 20 includes an accelerator 30 for generating a pulsed deuteron beam 32 and for directing the pulsed deuteron beam to a target 34. The beam 32 is on the order of 3.0 MeV to 8.0 MeV. The pulses of the deuteron beam 32 have a pulse length of about 1 nanosecond or less. The neutron source 20 is enclosed in shielding 38 which is in the shape of a sphere or the like with an aperture oriented so that only those neutrons that are heading in the direction of the sample object 29 are released from the shielding 38.

In one embodiment, the accelerator 30 is a small tandem accelerator with a terminal voltage of between 2.0 MeV and 2.5 MeV. The accelerator utilizes a negative ion source at ground potential and accelerates the negative ions to the energy of 2.0 MeV to 2.5 MeV. The ions are then doubly stripped and accelerated back to ground at the opposite end of the accelerator, gaining another 2 to 2.5 MeV, giving them a total energy of 4 MeV to 5 MeV.

The target 34 has a composition such that impingement of the pulsed deuteron beam 32 produces a pulsed white neutron beam 36. As used herein, the term "white neutron beam" means a beam of neutrons having energies in a range from approximately 0.5 MeV to at least 5.0 MeV. The beam has a relatively flat neutron distribution and is configured to approximate the shape of a cone in order to scan an entire sample object at the same time.

In the embodiment shown, the neutron detector array 40 is placed about three to six meters away from the target 34 along the flight path of the neutrons 36. The neutron detector array 40 is comprised of an θ-φ array 40 of neutron detector assemblies 22. The detector array 40 includes enough detectors to cover a large suitcase with a spatial resolution of 4 centimeters by 4 centimeters. Although not shown as such, shielding is provided around the detector array 40.

Figures 2A, 2B:
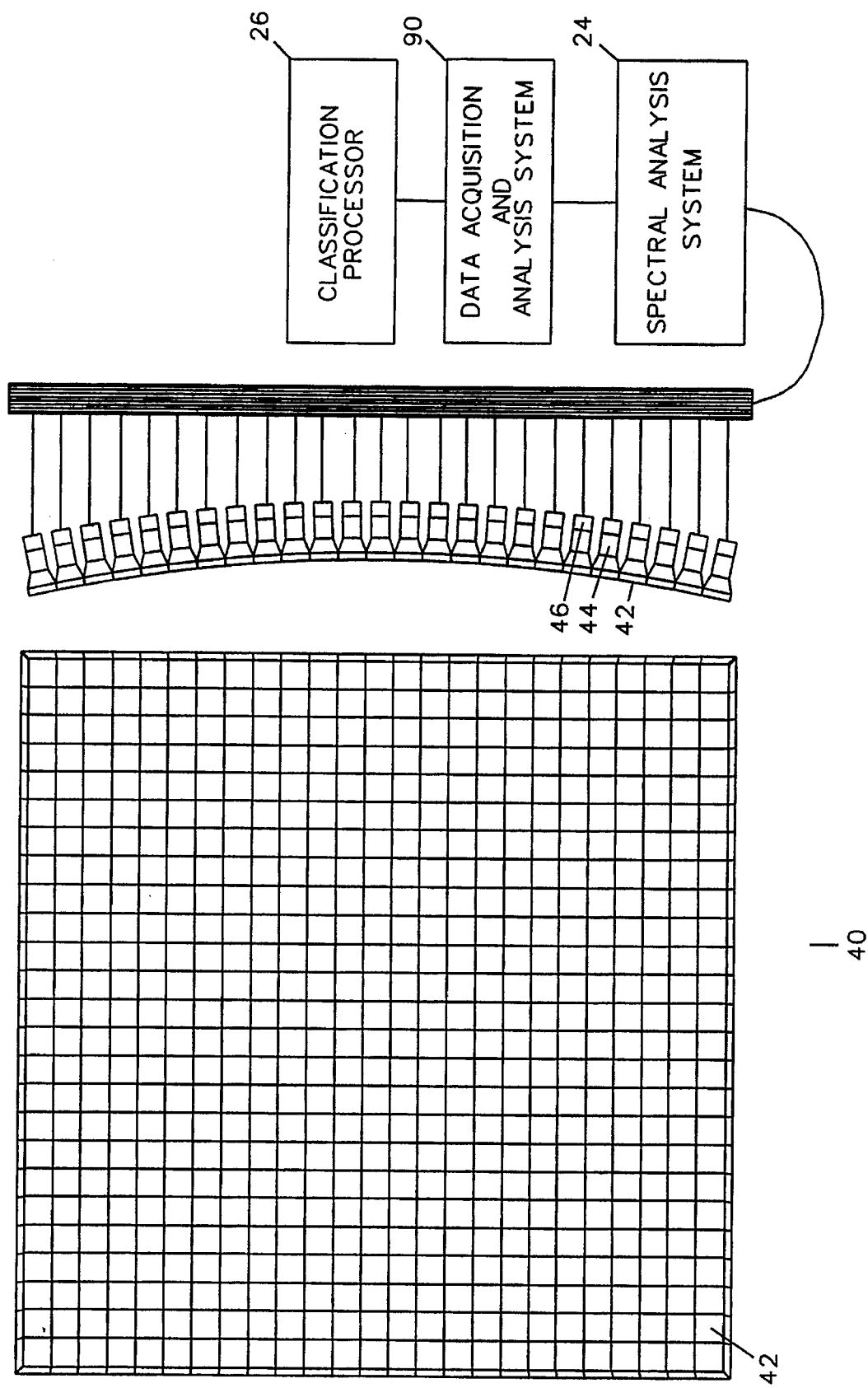
FIGS. 2a and 2b are views of the R-θ-φ (with constant R) detector of FIG. 1.

The particular detector array 40 shown in FIGS. 2a and 2b includes twenty-five columns of detector elements 42, with each column consisting of twenty-five detector elements 42. Thus, six hundred twenty-five neutron detector elements 42 are provided in the array 40. It should be understood that the array 40 may take on other sizes in accordance with the type of objects for which the contraband detection system is designed to operate.

Figure 3:
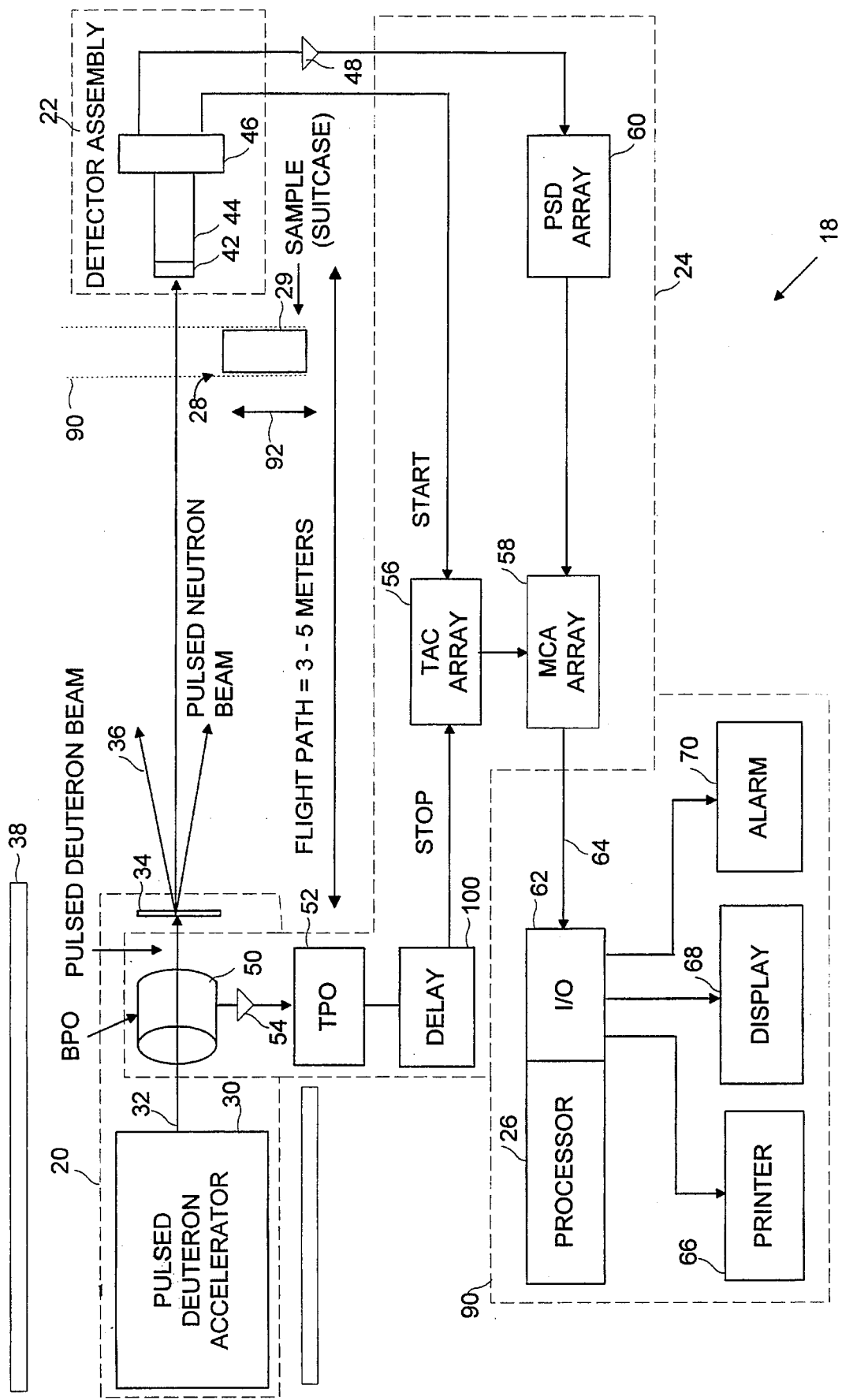
FIG. 3 shows a schematic of the electronics.

FIG. 3 shows a schematic diagram for the electronics.

The neutron detector assembly 22 is comprised of a neutron detector element 42, a photomultiplier tube 44, and a voltage divider 46. The photomultiplier tubes 44 have less than a nanosecond rise time and each voltage divider 46 is connected through an amplifier 48 to the spectral analysis system 24.

The spectra analysis system 24 includes a deuteron beam pick-off 50; a time pick-off controller 52; an amplifier 54; an array 56 of time-to-amplitude converters (TACs); a multi-channel analyzer array 58; and a pulse shape discrimination circuit array 60.

The neutron detector assembly 22 can acquire configurations other than that described above. For example, the detector elements 42, photomultipliers 44, and pulse shape discrimination circuit 60 can be replaced with scintillation and detection apparatus disclosed in my patent Miller (U.S. Pat. No. 5,155,366) Oct. 13, 1992, entitled Method and Apparatus for Detecting and Discriminating Between Particles and Rays, incorporated herein by reference.

The deuteron beam pick-off 50 is a cylinder which senses when a charged deuteron pulse travels through the cylinder. The electric current sensed by the beam pick-off 50 is amplified by the amplifier 54 and is sensed by the time pick-off 52. The signal from the beam pick-off 50 causes the time pick-off 52 to generate a real time "stop" pulse which is applied to each of a plurality of converters in the array 56 of time-to-amplitude converters.

Each of the time-to-amplitude converters included in the array 56 is associated with a corresponding one of the detector elements 42, and accordingly is associated with a corresponding one of the photomultiplier tubes 44. Each of the TAC units in array 56 is connected to receive a real time "start" pulse from the neutron detector assembly 22. Thus connected, each TAC in array 56 receives a real time stop pulse from the time pick-off 52 through a time delay 100 as the deuteron bunch travels through the beam pick-off 50. When a neutron impinges on one of the detector elements 42 and creates a measurable pulse in the neutron detector assembly 22, the impinged-upon detector 42, via its associated photomultiplier tube 44 and voltage divider 46, sends a real time "start" pulse to the associated TAC ("the activated TAC") in array 56. After the delayed stop pulse arrives at the activated TAC 56, the TAC 56 then generates a signal having an amplitude proportional to the time-of-flight from the beam pick-off 50 to the neutron detector element 42.

In order to make the TAC units in array 56 more efficient, other embodiments can use signals from the detector elements 42 as a stop signal and signals from the time pick-off as the start signal as is well known in the prior art.

The pulse shape discrimination circuit 60 includes a number of pulse shape discrimination circuits corresponding to the number of detector elements 42 included in the array 40. The pulse shape discrimination circuits in network 60 discriminate gamma rays from neutrons for the multi-channel analyzer array 56, resulting in reduced background.

The multi-channel analyzer array 58 includes a multi-channel analyzer (MCA) 58 for each converter in TAC array 56. For the embodiment illustrated in FIG. 3, there are 625 MCAs in array 58. Each MCA in array 58 is connected to receive the output amplitude signals from a corresponding converter in TAC array 56.

In view of the fact that the amplitude of the output signal from an activated TAC in array 56 reflects time-of-flight, the associated MCA in array 58 sorts the amplitude pulses from the activated TAC to give a time of flight spectrum for the activated TAC. The amplitude pulses are then categorized into channels, with each channel corresponding to a small range of neutron energies. Each multi-channel analyzer in array 58 generates outputs which are indicative of the number of counts for each channel.

The processor 26 is a conventional data processing system having a central processing unit, memory, an arithmetic logic unit, and an input/output interface/controller 62. The processor 26 has its input/output interface/controller 62 connected by bus 64 to the MCAs included in array 58 to receive the data utilized to generate the total neutron cross section spectra curve for each detector element 42 with respect to the sample object 29. As noted, the term "total neutron cross section" is the sum of the neutron absorption cross section and the neutron scattering cross section. The input/output interface/controller 62 of the processor 26 is also connected to a printer 66; to a CRT display screen 68; and to an alarm 70.

The central processing unit of the processor 26 executes instructions for evaluating the neutron attenuation spectra for the plurality of contraband-indicating elements. In this regard, as noted, the output of each MCA in array 58 is connected to the input/output controller 62 of the processor 26 by a corresponding line in bus 64. The processor 26 performs calculations for each of the MCAs included in the MCA system 58 in order to produce a neutron attenuation spectra corresponding to each of the detector elements 42 included in the array 40. The types of calculations performed by the processor 26 with respect to the data obtained from each of the MCAs included in array 58 for generating the spectra is in accordance with standard techniques such as those understood with reference to Marion and Fowler, *Fast Neutron Physics*, 1960.

Thus, the processor 26 creates neutron attenuation spectra for each neutron detector element 42 included in the neutron detector array 40. Data indicative of the neutron attenuation spectra for each detector element 42 is stored in memory and also ported to the printer 66. Still further, the processor 26 produces a graphic depiction of the neutron attenuation spectra for each neutron detector element 42. The graphic depiction is selectively displayable both on the CRT display screen 68 and on hardcopy output generated by the printer 66.

Numerous commercially available devices may be employed for the elements of the analysis system 24 of FIG. 3. For example, the time pick-off 52, amplifier 54 (as well as amplifiers 48), the TACs included in array 56, and the pulse shape discrimination circuits included in network 60 are available from Canberra as model numbers 2126, 2111, 2143, and 2160A, respectively. A suitable scintillator is a liquid scintillator manufactured by Nuclear Enterprises, Inc. as model NE-213. The photomultiplier tubes 44 can be any suitable commercially available tubes, such as those manufactured by Burle as model 8575, or the HAMAMATSU R2083. A suitable voltage divider 46 is manufactured by ORTEC as model 261.

The contraband detection system 18 of the present invention detects the presence of a plurality of contraband-indicative elements, including nitrogen, hydrogen, oxygen, and carbon. Of these contraband-indicative elements, in an energy range of interest, most will have peaks in their neutron attenuation spectra at energies at which neutrons are removed from the beam. To this end, operation of the contraband detection system 18 of the present invention is optimum if several peaks or distinguishing features, which are not overlapping, for the contraband-indicative elements are present. Although hydrogen does not have a peak, the amount of hydrogen can be ascertained using particular classification determination techniques, known as the matrix or regression techniques.

Figure 4:
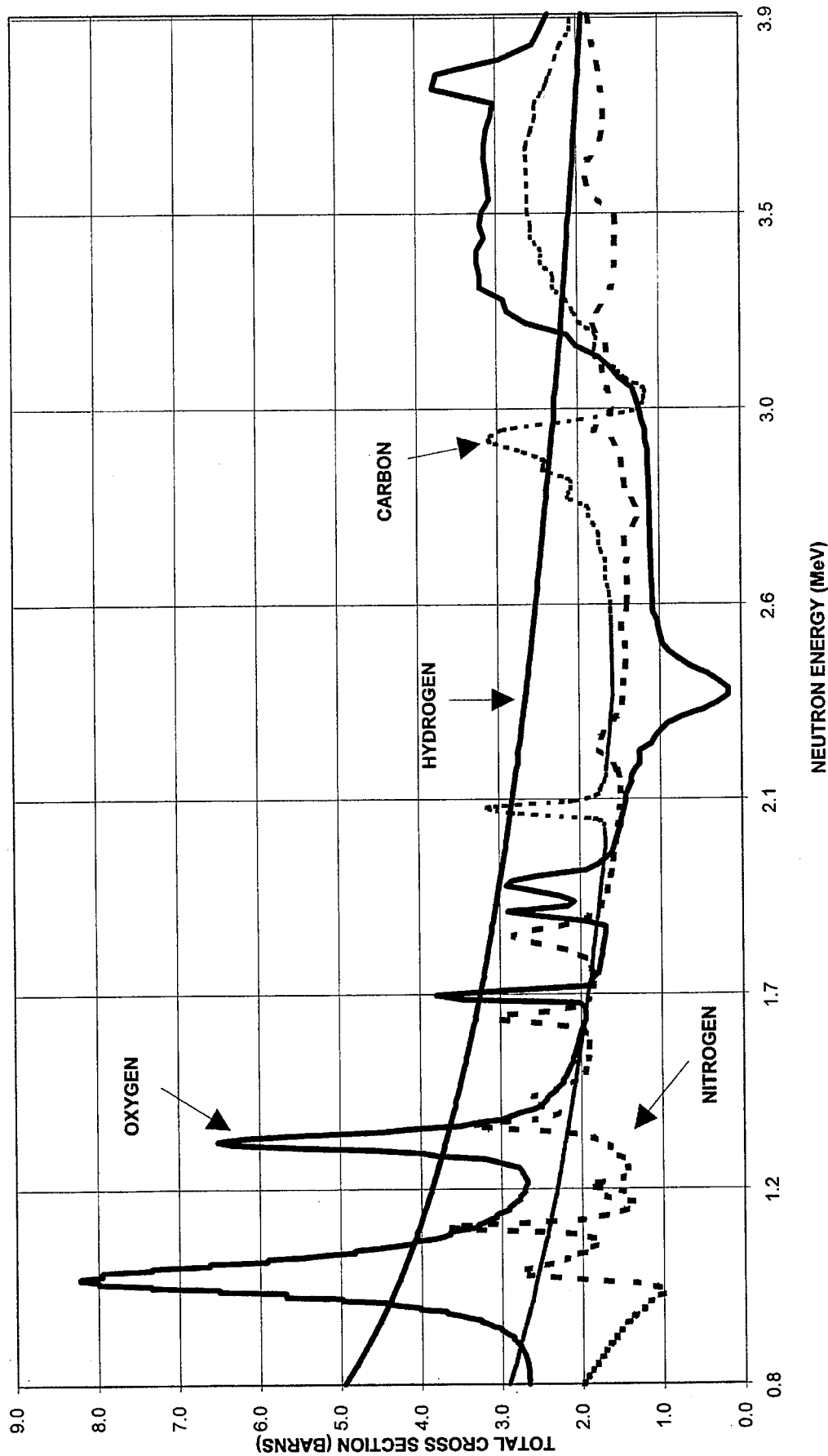
FIG. 4 is a graph showing total neutron cross section curves for hydrogen, carbon, nitrogen, and oxygen.

FIG. 4 is a graphic depiction of the superimposed total neutron cross section curves for hydrogen, carbon, nitrogen, and oxygen. The neutron cross section curves (Evaluated Nuclear Data Files) are available from Brookhaven National Laboratory and Oak Ridge National Laboratory. As shown in FIG. 4, there are several non-overlapping peaks for nitrogen, oxygen, and carbon.

The peaks shown in FIG. 4 correspond to neutron energies at which neutrons are absorbed and/or scattered (i.e., "removed" from a beam) by the respective elements. For example, carbon has one large neutron removal peak at 2.07 MeV and a smaller neutron removal peak at 2.9 MeV. Oxygen has a large doublet at 1.69 MeV and 1.65 MeV. Nitrogen has two prominent peaks, one on each side of the large oxygen doublet: 1.78 MeV and 1.6 MeV. There is another large oxygen peak located at 1.32 MeV with two nitrogen peaks too close to clearly resolve. There are three more nitrogen peaks located at 1.21 MeV, 1.18 MeV, and 1.12 MeV that can also be used. There is a large oxygen peak at 1 MeV.

Thus, if oxygen is present in a sample object, the presence of oxygen is signaled by the absorption and/or scattering of neutrons at the illustrated oxygen peaks. Similarly, the presence of carbon and nitrogen are indicated by the absorption and/or scattering of neutrons at the respective peaks.

In addition to generating the neutron attenuation spectra for each of the detector elements 42, the central processing unit of the processor 26 includes instructions, which, when executed, make a classification determination regarding a potential contraband substance located by each detector 42 in the sample object 29. When a detector element 42 locates elements in sample object 29 for which the processor 26 makes a contraband classification determination, the processor outputs a signal to the alarm device 70. There are several possible modes for making a classification determination.

It is thus understood that the contraband detection system 18 of the present invention analyzes the neutron attenuation spectra for three elements (C, N, and O) which have neutron-removal peaks in the range of fast neutron energies, and a further element (H) which does not have a neutron-removal peak in the range of fast neutron energies.

The processor 26 can utilize software including regression theory to determine not only the number of atoms per square centimeter for each of the contraband-indicating elements, but also a standard error associated with each element. An example of such software is Excel for Windows produced by Microsoft, which provides regression theory capability in connection with its advanced mathematical tools.

To determine the number densities of the sample, known total neutron cross sections for each element for each energy in the energy range of interest are supplied to the processor 26 as independent variables. For each detector element 42, values of ln ($N_o/N$), with the N values having been obtained from the associated MCA in array 58, are supplied to the processor 26 as dependent variables. The processor 26 then outputs, for each detector element 42, the number of atoms per square centimeter for each contraband-indicating element, as well as the standard error for each of the contraband indicating elements.

Figure 5:
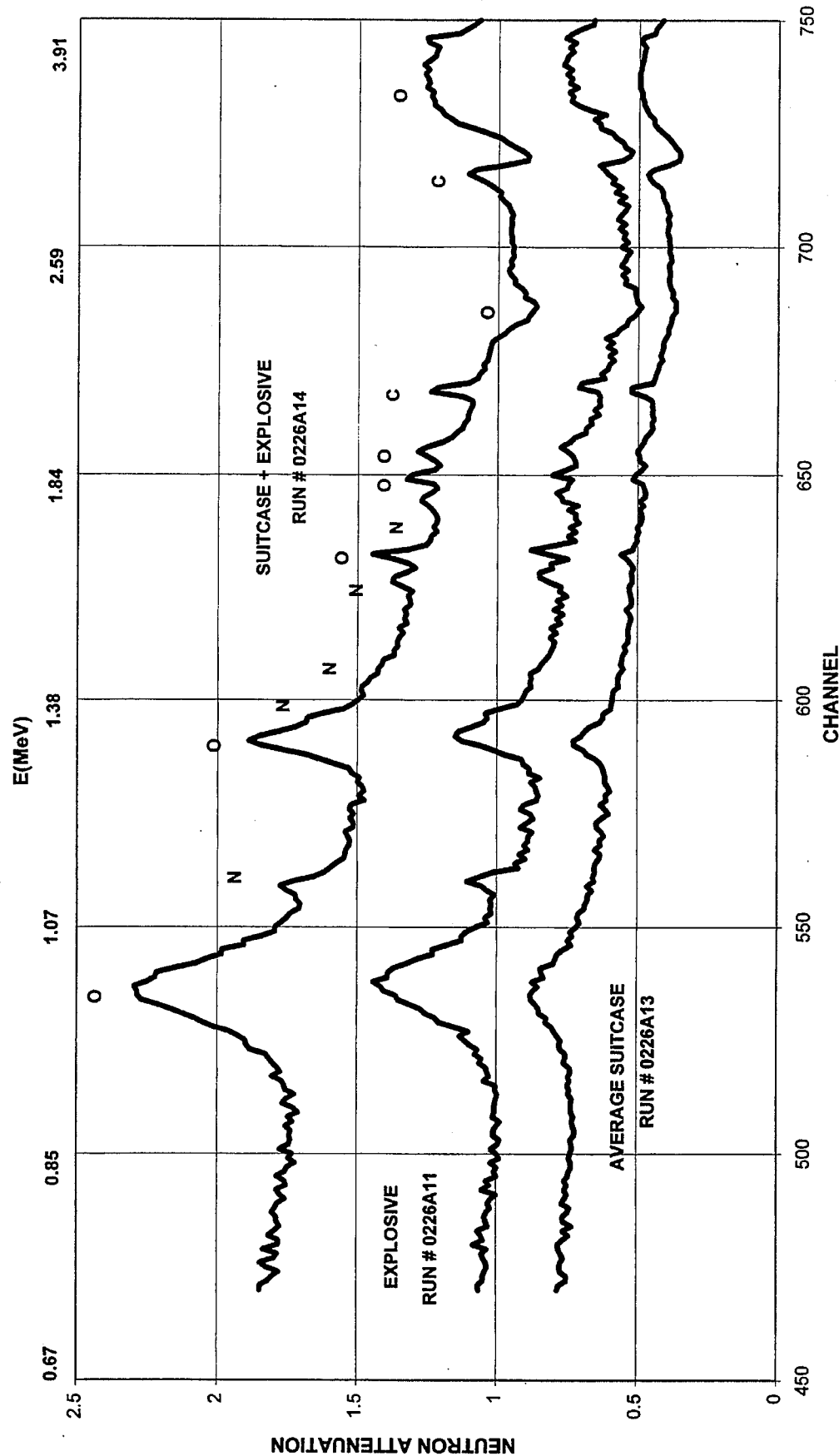
FIG. 5 is a graph showing the neutron attenuation of an average suitcase, a 4 cm thick piece of the explosive C-4, and the explosive C-4 imbedded in an average suitcase.
Figure 6:
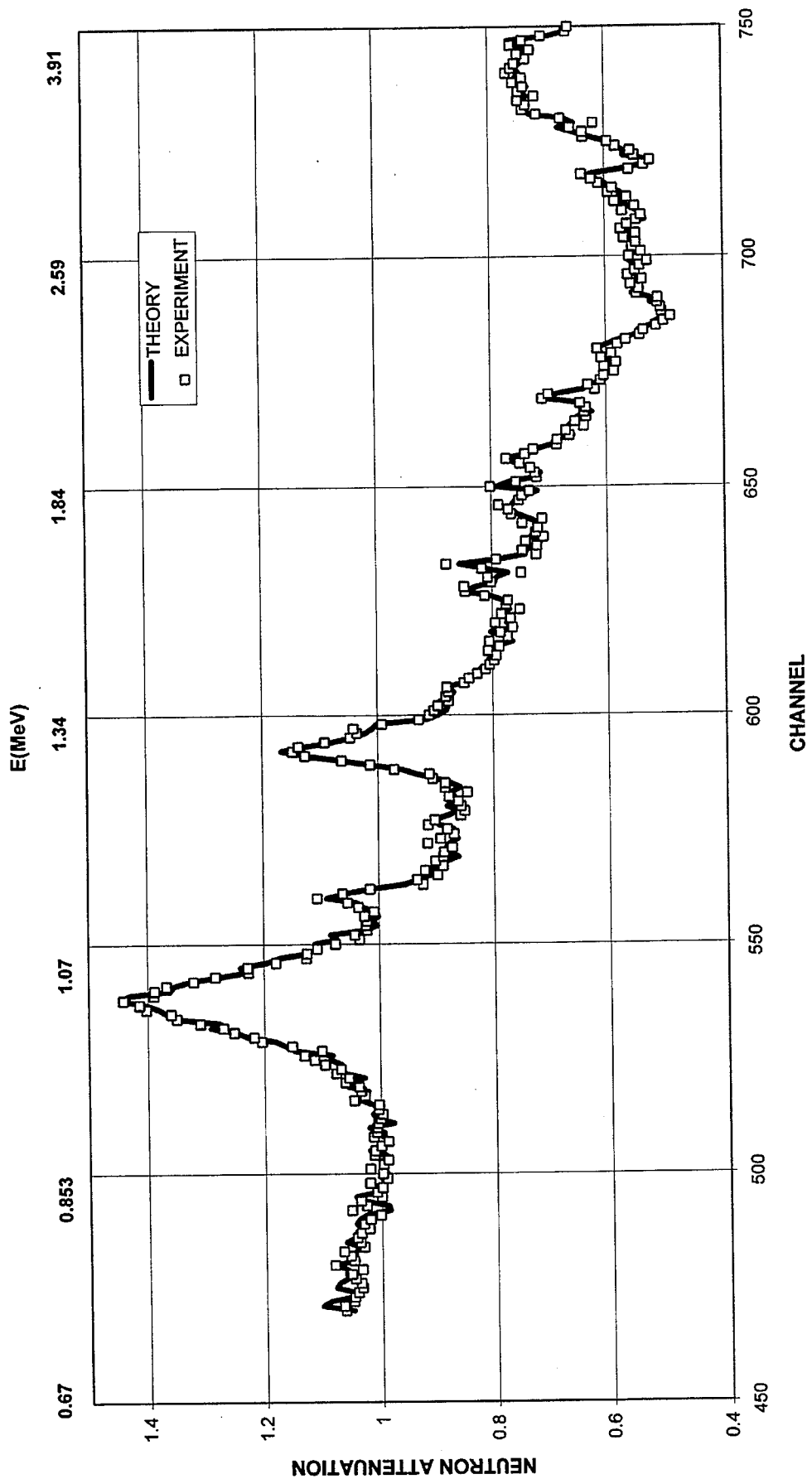
FIG. 6 shows a linear regression theory fit to the measured C-4 neutron attenuation curve of FIG. 5.

The total cross sections used as the independent variable can be obtained from the ENDF cross sections and approximately "smeared" to fit the energy resolution of the spectrometer or they could be measured with the spectrometer. It has been found by the author of this patent that measuring the total cross sections with the neutron spectrometer gives the best results. T. G. Miller, "Application of Fast Neutron Scattering Spectroscopy (FNS/R) to Airport Security," SPIE Vol. 1737 Neutrons, X-rays and Gamma Rays (1992). FIG. 4 shows a graph of the total cross sections of H, C, N and O. FIG. 5 shows a graph of the measured neutron attenuation of an "average" suitcase, 4 cm of the explosive C-4, and 4 cm of the explosive C-4 imbedded in an "average" suitcase. The various peaks of C, N, and O are indicated. As can be seen from FIG. 4, adding the explosive to the suitcase dilutes the pure explosive spectrum to some extent, but most of the features of the explosives attenuation spectrum are maintained. FIG. 6 shows a regression theory fit to the C-4 attenuation curve of FIG. 5. As can be seen, the fit is good. FIG. 7 gives the regression theory statistics for the curve fit of FIG. 6. FIG. 7 gives an R-Squared of 0.997 and, as can be seen, the number densities of H, C, N and O are all determined with a standard error of less than 0.7%.

For each detector, the resultant number of atoms per square centimeter for each of the four elements N, C, H, and O can be further examined to determine whether the degree of presence of these elements indicates that contraband is concealed in a suitcase. In this respect, the resultant numbers can be evaluated using atomic ratio expressions, (C/O, N/O and H/C), where the experimentally determined ratios are compared to the ratios of explosives, and a determination is made. It has been shown by the author of this patent that neural networks can be used to quickly optimize such data for the presence of explosives. "Decision Making Using Conventional Calculations Versus Neural Networks for Substance Identification," T. Gill Miller, SPIE Vol. 2093, pp. 182–193 (1993).

Thus, by using the stored data which is available to the processor 26, the processor 26 can determine whether the suitcase contains polyurethane and other similar plastics and can also determine the type of explosive or plastic in the suitcase. When the processor 26 determines that any detector element 42 has detected contraband in accordance with the classification mode described above, the processor 26 activates the alarm 70 in the manner already described.

While the invention has been particularly shown and described with reference to the preferred embodiments thereof, it will be understood by those skilled in the art that various alterations in form and detail may be made therein without departing from the spirit and scope of the invention. For example, the presence of elements other than N, C, H, and O can be detected. In this regard, the known total neutron cross sections of other elements can be included in the calculations to obtain an indication of the presence of those elements in the sample object.

The embodiments of the invention in which an exclusive property or privilege is claimed are defined as follows:

1. Apparatus for detecting a contraband substance internally located in a sample object, wherein all portions of the sample object may be analyzed simultaneously through the use of a single beam of neutrons, the apparatus comprising:

means for producing a pulsed beam of fast white neutrons from a point source, which beam expands to a conical shape and has sufficient intensity in a range over several MeV, so that a plurality of elements have one or more resonance peaks in such energy range;

means for detecting neutrons, which means includes one or more neutron detectors;

means for measuring the time of flight of neutrons from said point source to the said detecting means;

means for situating a sample object between the neutron producing means and the detecting means at a point at which the said neutron beam has expanded sufficiently to allow neutrons in the beam to contact all portions of the sample object sought to be analyzed;

means for determining the neutron attenuation spectra of each portion of the sample object encompassing a solid angle between said point source and a detector of the said detector means; and means for making a classification determination based upon said neutron attenuation spectra regarding a potential contraband substance located in the sample object.

2. The apparatus of claim 1, wherein the means for detecting neutrons comprises neutron detectors configured to form a curved surface, so that each said detector is on a straight line and approximately equidistant from the said white neutron point source.

3. The apparatus of claim 1, further comprising processing means for evaluating the neutron attenuation spectra for each portion of the sample object encompassing a solid angle between said point source and a detector of the said detector means for the plurality of contraband-indicating elements, by using the measured attenuation spectra and the total cross sections of the elements in the sample object and determining or imaging the concentrations or number densities of a plurality of elements located in the sample object, and for making a classification determination regarding a potential contraband substance located in the sample object.

4. The apparatus of claim 1, further comprising processing means for evaluating the neutron attenuation spectra for each portion of the sample object encompassing a solid angle between said point source and a detector of the said detector means for the plurality of contraband-indicating elements, including elements which do not have a resonance peak in the energy range of said neutron beam such as hydrogen, and determining or imaging the concentrations or number densities of a plurality of elements located in the sample object, and for making a classification determination regarding a potential contraband substance located in the sample object.

5. The apparatus of claim 1, wherein the said means for determining the neutron attenuation spectra consists of a central processing unit which executes instructions for taking the natural log of the ratios of the neutron flux of the beam (as a function of neutron energy) when the sample object is not in the beam and the neutron flux of the beam (as a function of neutron energy) when the sample object is in the beam.

6. The apparatus of claim 1, wherein the said means of making the classification determination regarding the presence of a contraband substance consists of one or more neural networks trained to recognize neutron attenuation spectra of objects containing contraband substances.

7. Apparatus for detecting a contraband substance internally located in a sample object, the apparatus comprising:

(1) means for producing a pulsed beam of fast white neutrons from a point source in an energy range over several MeV, so that a plurality of elements, including but not limited to carbon, nitrogen, and oxygen, have one or more resonance peaks in such energy range;

(2) means for detecting neutrons, including neutrons in the said white neutron beam, with or without a sample object in said beam, and for determining which neutrons are not removed from the beam when a sample object is in the beam;

(3) means for situating a sample object between the neutron producing means and the detecting means;

(4) means for evaluating the neutron attenuation spectra for the sample object; and, (5) processing means for evaluating the neutron attenuation spectra to determine the potential presence of hydrogen in the sample object, or the presence of other elements in the sample object which do not have a resonance peak in the energy range of interest, where the processing means further uses the neutron attenuation spectra evaluation and the determination of the potential presence of hydrogen or other such element not containing a resonance peak to make a classification determination regarding a potential presence of a contraband substance located in the sample object.

8. The apparatus of claim 7, wherein the means for detecting neutrons comprises neutron detectors, configured to form a curved surface, so that each said detector is on a straight line and approximately equidistant from the said white neutron point source.

9. The apparatus of claim 7, wherein the processing means uses the said neutron removal spectra evaluation and the determination of the potential presence of hydrogen, or another element which does not have a resonance peak in the energy range of interest, to make a classification determination regarding a potential presence of a contraband substance located in the sample object, through evaluating the following expression:

$$\left( \mathrm{Ln} \frac{N_o}{N} \right)_{C_i} = \left( \sum_j \sigma_j \alpha_j \right)_{C_i}$$

Where:

$N_o$=Neutron spectra without sample object in neutron beam $N$=Neutron spectra with sample object in neutron beam $C_i$=$i^{th}$ Channel of the multi-channel analyzer $\sigma_j$=Total cross sections of the $j^{th}$ element $\alpha_j$=Atoms per cm$^2$ of $j^{th}$ element in the neutron beam, using linear regression or other method to evaluate $\alpha$, wherein the number of elements is given by j and where $\alpha_1$ represents the number density of hydrogen, or another element which does not have a resonance peak in the energy range of interest, and the remaining $\alpha_j$ represent the number densities of other contraband indicating elements; for example without limitation $\alpha_1$ would represent the number density of hydrogen atoms density per square cm, $\alpha_2$ could represent the number density of carbon in atoms per square cm, $\alpha_3$ could represent the number density of nitrogen atoms in per square cm, and $\alpha_4$ could represent the number density of oxygen in atoms per square cm in the neutron beam;

processing means for determining the atomic ratios of contraband-indicating elements, including without limitation C/O, N/O, H/C, and NO/CH;

processing means for determining if said measured atomic ratios match or approximate the same atomic ratios of such elements in known contraband substances; and means for sounding an alarm to denote the presence of contraband if said measured atomic ratios match or approximate the same atomic ratios of such elements in known contraband substances.

10. Method of detecting a contraband substance internally located in a sample object, comprising the steps of measuring the neutron attenuation spectra of all portions of a sample object simultaneously, evaluating said neutron attenuation spectra, and making a classification determination on the basis of such neutron attenuation spectra regarding whether there is a contraband substance internally located in the sample object.

11. The method of claim 10, wherein the step of measuring said neutron attenuation spectra includes producing a pulsed white neutron beam which has sufficient intensity in a range over several MeV so that a plurality of contraband-indicating elements have one or more resonance peaks in such energy range and which beam is caused to expand from a point source in a conical shape to encompass the portions of the sample object sought to be analyzed; configuring a plurality of neutron detectors to form a curved surface such that each such neutron detector is on a straight line and approximately equidistant from said point source; measuring the time of flight of neutrons in said beam from said point source to said detectors; and determining the neutron attenuation spectra on the basis of such time of flight measurements.

12. The method of claim 11, wherein the step of measuring said neutron attenuation spectra includes measuring the neutron flux of the beam (as a function of neutron energy) when the sample object is not in the beam and measuring the neutron flux of the beam (as a function of neutron energy) when the sample object is in the beam, and then taking the natural log of the ratios of such neutron flux measurements to determine the neutron attenuation spectra.

13. The method of claim 10, wherein the steps of evaluating the neutron spectra and making a classification determination regarding the presence of a contraband substance are performed by one or more neural networks trained to recognize attenuation spectra of objects containing contraband substances.

14. The method of claim 10, wherein the step for evaluating the neutron spectra includes determining or imaging the number densities of the atoms of a plurality of contraband-indicating elements located in the sample object, including hydrogen or other elements which do not have a resonance peak in the energy range of interest, based upon said neutron attenuation spectra and wherein the step of making said classification determination includes comparing the ratios of said number densities of the contraband-indicating elements in such sample object with the known number density ratios of such elements in contraband substances.

15. The method of claim 10, wherein the step of evaluating said neutron attenuation spectra includes using such neutron attenuation spectra along with known total cross sections of contraband-indicating elements to determine or image the number densities of contraband-indicating elements in the sample object, and wherein the step of making the said classification determination includes comparing the measured number densities of contraband-indicating elements in the sample object to known number densities of such elements in contraband substances.

16. The method of claim 10, wherein the step of evaluating said neutron attenuation spectra includes determining the number densities of contraband-indicating elements in the sample object which do not have a resonance peak in the energy range of said neutron beam, such as hydrogen, and the step of making a classification determination regarding a potential contraband substance includes using the absence or presence and amount of hydrogen in the sample object as a basis for the classification determination.

17. The method of claim 10, wherein the step of evaluating the said neutron attenuation spectra includes using known total cross sections of contraband-indicating elements to determine the number densities of elements in the said sample object by using the following expression:

$$\left( \mathrm{Ln} \frac{N_o}{N} \right)_{C_i} = \left( \sum_j \sigma_j \alpha_j \right)_{C_i}$$

Where:
$N_o$=Neutron spectra without sample object in neutron beam
$N$=Neutron spectra with sample object in neutron beam
$C_i$=$i^{th}$ Channel of the multi-channel analyzer
$\sigma_j$ =Total cross sections of the $j^{th}$ element
$\alpha_j$=Atoms per cm$^2$ of $j^{th}$ element in the neutron beam
using linear regression or other method known in the prior art to evaluate $\alpha$, wherein the number of elements is given by $j$ and where $\alpha_1$ represents hydrogen, or another element which does not have a resonance peak in the energy range of interest, and the remaining $\alpha_j$ represent the number densities of other contraband-indicating elements, and thereby obtaining the number densities of contraband-indicating elements located in the sample object; and wherein the step of making a classification determination includes determining the various ratios of H, C, N, and O contained in the sample object, including without limitation C/O, N/O, H/C, and NO/CH, and comparing said measured atomic ratios to known atomic ratios of such contraband-indicating elements in known contraband substances.

18. Method of detecting a contraband substance internally located in a sample object, comprising the steps of measuring the neutron attenuation spectra of all portions of a sample object, evaluating said neutron attenuation spectra to identify contraband-indicating elements which do not have a resonance peak in the energy range of said neutron attenuation spectra, including hydrogen, and making a classification determination on the basis of such neutron attenuation spectra and absence or presence and amount of said elements which do not have a resonance peak within the energy ranges in said attenuation spectra, including hydrogen, regarding whether there is a contraband substance internally located in the sample object.

19. Apparatus for detecting a contraband substance internally located in a sample object, wherein all portions of the sample object may be analyzed simultaneously through the use of a single beam of neutrons, the apparatus comprising:

(i) an accelerator for generating a pulsed deuteron beam and for directing the pulsed deuteron beam to a target;

(ii) a target with a composition such that impingement of the pulsed deuteron beam produces a single pulsed beam of neutrons which expands in a conical shape from a point source;

(iii) a neutron detector array;

(iv) a conveying system for introducing a sample object, such as a suitcase, between the neutron source and the neutron detector assembly;

(v) a spectra analysis system; and (vi) a processor for evaluating the said neutron attenuation spectra for the plurality of contraband-indicating elements and for making a classification determination regarding a potential contraband substance located in the sample object.

20. The apparatus of claim 19, wherein the said accelerator is capable of producing a pulsed deuteron beam from 4–7 MeV with a beam width of 1 nanosecond with a repetition rate of 1–3 MHz: the said target consists of a composition such that impingement of the pulsed deuteron beam produces a pulsed white neutron beam with a relatively flat neutron distribution around 0 degrees which expands in the shape of a cone; the said neutron detector array is comprised of an θ-φ array of a plurality of neutron detector assemblies, wherein each such assembly is comprised of a neutron detector element, a photomultiplier tube, and a voltage divider connected through an amplifier to a spectral analysis system; the said spectra analysis system consists of a deuteron beam pick-off, a time pick-off, an array of time-to-amplitude converters (TACs), a multi-channel analyzer array, and a background gamma ray reduction circuit; and the said processor consists of a conventional data processing system having a central processing unit, memory, an arithmetic logic unit, and an input/output interface/controller which is connected to a printer, a CRT display screen, and an alarm.

* * * * *